(12) United States Patent
Childer et al.

(10) Patent No.: US 7,467,630 B2
(45) Date of Patent: Dec. 23, 2008

(54) MEDICAMENT DISPENSER

(75) Inventors: Winthrop D. Childer, San Diego, CA (US); David Tyvoll, La Jolla, CA (US); Douglas A. Sexton, La Jolla, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 796 days.

(21) Appl. No.: 10/777,449

(22) Filed: Feb. 11, 2004

(65) Prior Publication Data

US 2005/0172957 A1    Aug. 11, 2005

(51) Int. Cl.
  *A61M 11/00* (2006.01)
  *A61M 15/00* (2006.01)
  *A61M 16/00* (2006.01)
  *B05D 7/14* (2006.01)
  *B65D 83/06* (2006.01)

(52) U.S. Cl. ............... 128/200.23; 128/203.15

(58) Field of Classification Search ............ 128/200.14, 128/200.23, 203.12–203.14, 203.17; 73/1.74, 73/1.36; 222/71; 29/407.05
See application file for complete search history.

(56) References Cited

U.S. PATENT DOCUMENTS

| | | |
|---|---|---|
| 4,542,650 A | 9/1985 | Renken et al. |
| 4,776,214 A | 10/1988 | Moran et al. |
| 4,853,717 A | 8/1989 | Harmon et al. |
| 4,967,208 A | 10/1990 | Childers |
| 4,969,357 A | 11/1990 | Mickler |
| 5,035,138 A | 7/1991 | Abdel-Rahman |
| 5,103,244 A | 4/1992 | Gast et al. |
| 5,108,193 A | 4/1992 | Furubayashi |
| 5,115,250 A | 5/1992 | Harmon et al. |
| 5,209,111 A | 5/1993 | Agarwal et al. |
| 5,237,866 A | 8/1993 | Nijdam |
| 5,278,626 A * | 1/1994 | Poole et al. ............ 356/36 |
| 5,284,133 A | 2/1994 | Burns et al. |
| 5,331,953 A | 7/1994 | Andersson et al. |
| 5,363,842 A | 11/1994 | Mishelevich et al. |
| 5,372,040 A | 12/1994 | Hecht et al. |
| 5,404,871 A | 4/1995 | Goodman et al. |
| 5,415,029 A | 5/1995 | Uchiyama et al. |
| 5,450,336 A | 9/1995 | Rubsamen et al. |
| 5,469,750 A | 11/1995 | Lloyd et al. |
| 5,500,660 A | 3/1996 | Childers et al. |
| 5,511,415 A | 4/1996 | Nair et al. |
| 5,515,295 A | 5/1996 | Wang |
| 5,524,084 A | 6/1996 | Wang et al. |
| 5,563,638 A | 10/1996 | Osborne |
| 5,608,647 A | 3/1997 | Rubsamen et al. |
| 5,621,441 A | 4/1997 | Waschhauser et al. |
| 5,676,129 A | 10/1997 | Rocci, Jr. et al. |
| 5,692,492 A | 12/1997 | Bruna et al. |

(Continued)

FOREIGN PATENT DOCUMENTS

EP    1 066 850 A1    1/2001

(Continued)

*Primary Examiner*—Justine R Yu
*Assistant Examiner*—Kristen C Matter

(57) ABSTRACT

A medicament dispenser that includes a medicament supply, an ejector, and a controller configured to actuate the ejector, where the controller is configured to use an operational parameter to produce a plurality of medicament drops having a target drop characteristic, and the operational parameter includes a correction factor that is based on a performance characteristic of the ejector.

26 Claims, 3 Drawing Sheets

U.S. PATENT DOCUMENTS

| | | | |
|---|---|---|---|
| 5,721,257 A | 2/1998 | Baker et al. | |
| 5,724,957 A | 3/1998 | Rubsamen et al. | |
| 5,726,357 A | 3/1998 | Manaka | |
| 5,780,736 A | 7/1998 | Russell | |
| 5,812,157 A | 9/1998 | Nguyen et al. | |
| 5,869,758 A | 2/1999 | Huiberts | |
| 5,880,748 A | 3/1999 | Childers et al. | |
| 5,881,716 A | 3/1999 | Wirch et al. | |
| 5,894,841 A | 4/1999 | Voges | |
| 5,925,021 A | 7/1999 | Castellano et al. | |
| 5,929,333 A | 7/1999 | Nair | |
| 5,952,571 A | 9/1999 | Arai et al. | |
| 5,992,990 A | 11/1999 | Childers et al. | |
| 6,029,659 A | 2/2000 | O'Connor | |
| 6,131,566 A | 10/2000 | Ashurst et al. | |
| 6,138,669 A | 10/2000 | Rocci, Jr. et al. | |
| 6,158,431 A | 12/2000 | Poole | |
| 6,162,443 A | 12/2000 | Flament-Garcia et al. | |
| 6,186,956 B1 | 2/2001 | McNamee | |
| 6,192,882 B1 | 2/2001 | Gonda | |
| 6,196,218 B1 | 3/2001 | Voges | |
| 6,196,219 B1 * | 3/2001 | Hess et al. | 128/200.21 |
| 6,220,243 B1 | 4/2001 | Schaeffer et al. | |
| 6,221,653 B1 | 4/2001 | Caren et al. | |
| 6,223,746 B1 | 5/2001 | Jewett et al. | |
| 6,224,897 B1 | 5/2001 | Reitberg | |
| 6,234,167 B1 * | 5/2001 | Cox et al. | 128/200.14 |
| 6,257,690 B1 | 7/2001 | Holstun | |
| 6,280,012 B1 | 8/2001 | Schloeman et al. | |
| 6,325,475 B1 | 12/2001 | Hayes et al. | |
| 6,328,405 B1 | 12/2001 | Weber et al. | |
| 6,378,988 B1 | 4/2002 | Taylor et al. | |
| 6,390,453 B1 | 5/2002 | Frederickson et al. | |
| 6,443,146 B1 | 9/2002 | Voges | |
| 6,460,537 B1 | 10/2002 | Bryant et al. | |
| 6,601,776 B1 | 8/2003 | Oljaca et al. | |
| 6,629,456 B2 | 10/2003 | Kohno | |
| 7,072,738 B2 * | 7/2006 | Bonney et al. | 700/237 |
| 2002/0109744 A1 | 8/2002 | Shindo | |
| 2002/0185125 A1 | 12/2002 | Klimowicz et al. | |
| 2003/0072717 A1 | 4/2003 | Reinhold et al. | |
| 2003/0101991 A1 | 6/2003 | Trueba | |

FOREIGN PATENT DOCUMENTS

| | | |
|---|---|---|
| EP | 1 452 199 A1 | 9/2004 |
| WO | WO 97/18846 | 5/1997 |
| WO | WO 99/37347 | 7/1999 |

* cited by examiner

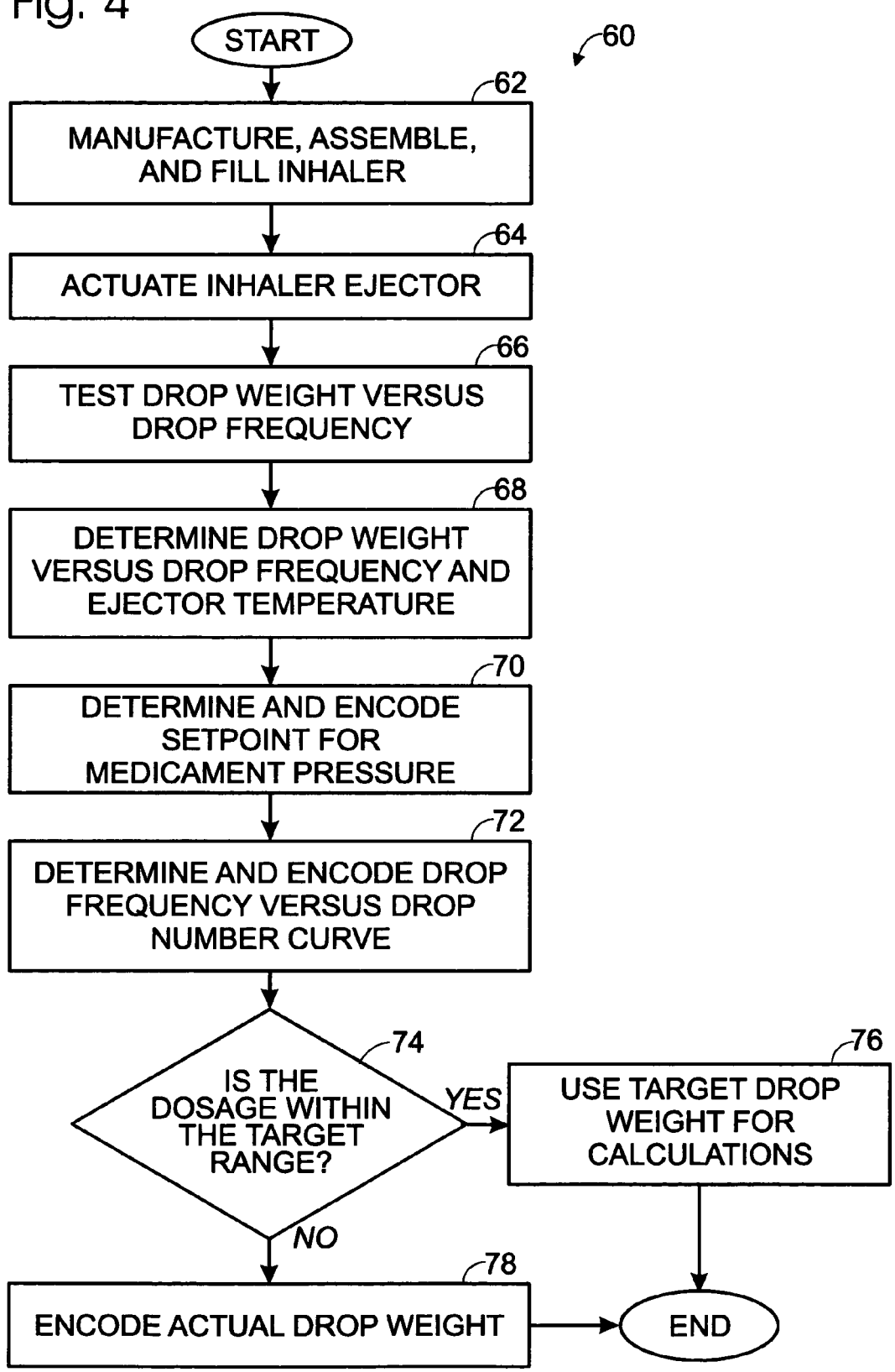

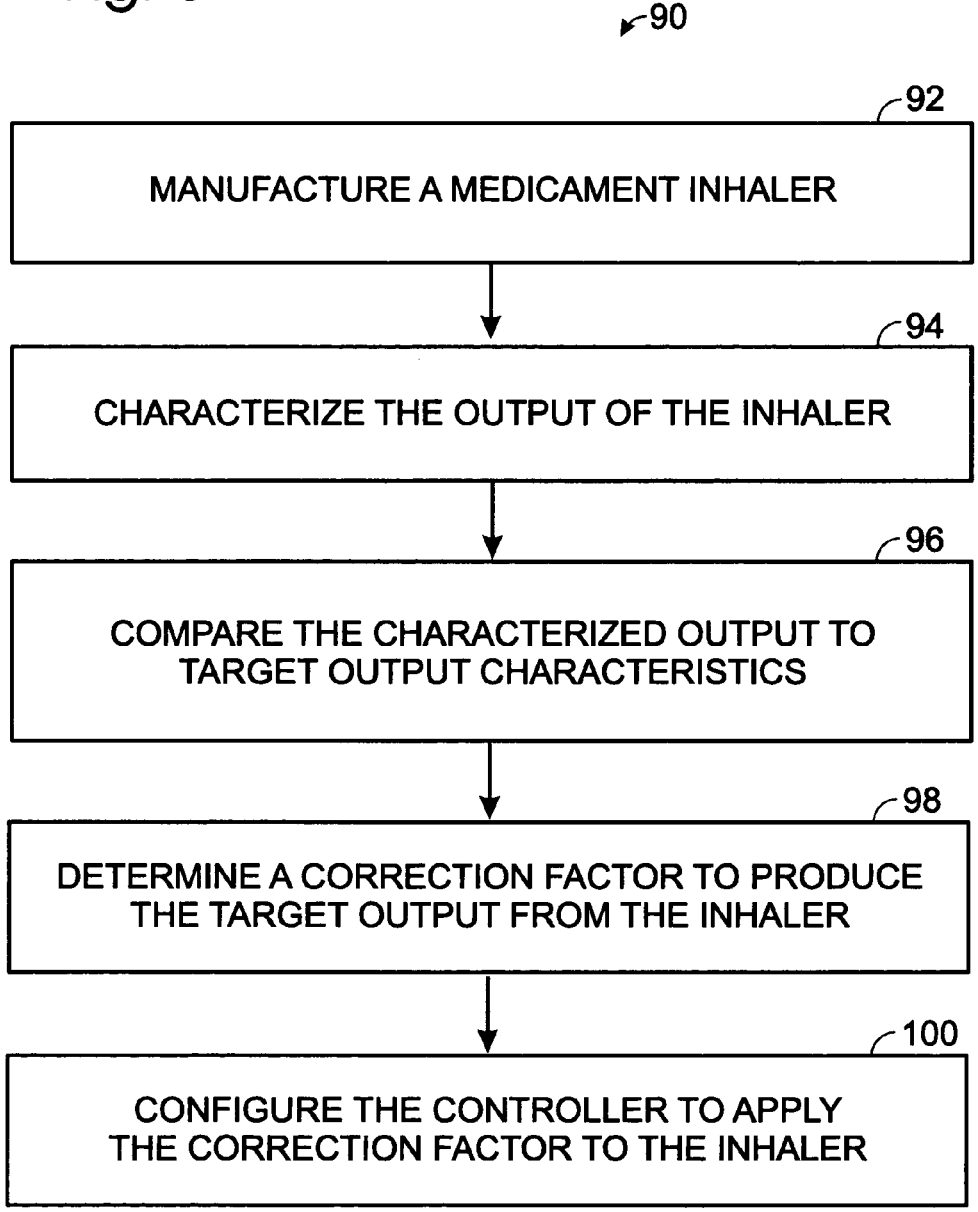

MEDICAMENT DISPENSER

BACKGROUND

Inhalers provide an alternative drug-delivery method that permits patients to aspirate medication rather than swallow a pill, or drink or inject medication. In some cases, such as with medications that directly target the patient's lungs, aspiration enables the medicine to reach the target area more quickly. In addition, aspiration may be less painful than other drug-delivery methods.

Many inhalers rely upon mechanical atomizers or pressurized cartridges to dispense medication. The dose delivery of such mechanisms can be dependent upon the force exerted on the activation mechanism, the pressure of carrier gas, and the inhalation force exerted by the user.

As an alternative, electronic inhalers, such as those that utilize plural drop ejectors to dispense medication, may be used. However, the drop volume produced by a given ejector mechanism may vary significantly from the manufacturing target value. This uncertainty in ejected drop volume may result in uncertainty in medication dosage. Furthermore, drop volume may determine where in the pulmonary system drops are absorbed.

BRIEF DESCRIPTION OF THE DRAWINGS

FIG. 4 is a flowchart depicting a process of calibrating an inhaler, according to an embodiment of the invention.

FIG. 5 is a flowchart depicting a process of calibrating an inhaler, according to an embodiment of the invention.

DETAILED DESCRIPTION

Figure 1:
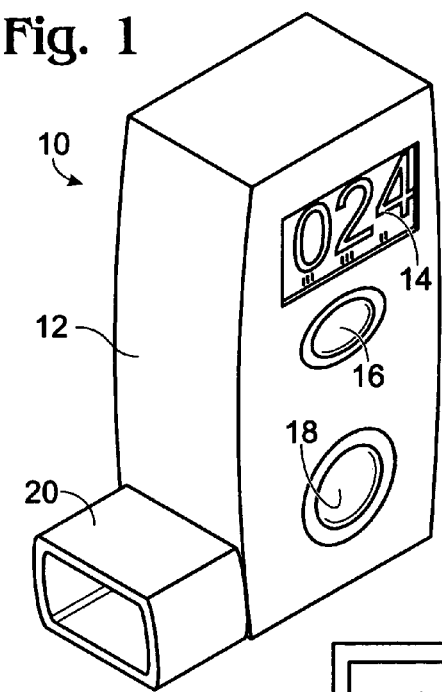
FIG. 1 depicts an inhaler according to an embodiment of the invention.

Referring initially to FIG. 1, an inhaler according to an embodiment of the present invention is shown at 10. Inhaler 10 includes a body 12 that may enclose the inhaler apparatus. As will be appreciated upon reading further, inhaler 10 may be configured to effect ejection of a selected dosage of medicament/inhalant therefrom in response to a signal sent by a controller. Suitable medicaments include those typically found in liquid, solid, powder, paste or other forms.

Inhaler 10 may include a display 14 that is configured to provide information to the user of the inhaler, such as the number of doses administered, the number of doses remaining in the inhaler, and/or the dosage that will be provided by the inhaler upon activation. Display 14 may also be adapted to provide the user with information such as patient name, patient identification number, prescribing physician name, prescribing physician identification number, type of medication, recommended dosage, dose regimen, available alterations to the recommended dosage and/or dose regimen, etc. As will be appreciated, display 14 may be located in any convenient location on body 12.

The inhaler may include one or more input mechanisms, such as a depressible button 16, configured to permit the user to select the information to be displayed by display 14, or to modify the operating parameters of the inhaler. For example, pushing button 16 may permit the user to change the operator parameter currently displayed, and/or change the dosage delivered by the inhaler. Inhaler 10 may further include an actuator, such as a depressible button 18, that, when triggered, results in the ejection of a dose of medicament in a form appropriate for inhalation by the user via a mouthpiece 20. Button 18 could alternatively take the form of a trigger, a switch, or a touch-sensitive screen, among others. Button 16 and/or button 18 may be located on a side of the inhaler body, as shown, or may be positioned in virtually any other location convenient to the user.

It will be appreciated that mouthpiece 20 may take alternative forms according to the particular medicament dispensed, the age of the user, and the medical treatment being implemented, including for example, forms which may be adapted to fit over a user's mouth and/or nose. Alternatively, or in addition, the inhaler may be fitted with a spacer device disposed between the inhaler apparatus and the mouthpiece, for example including a holding chamber. In addition, body 12 may be shaped to provide regions to accommodate the hand and/or fingers of the user. The present disclosure is not limited to L-shaped inhalers, as shown in FIG. 1, but may also include linear inhaler designs, wherein the inhaler body extends longitudinally along the same axis as the mouthpiece.

Figure 2:
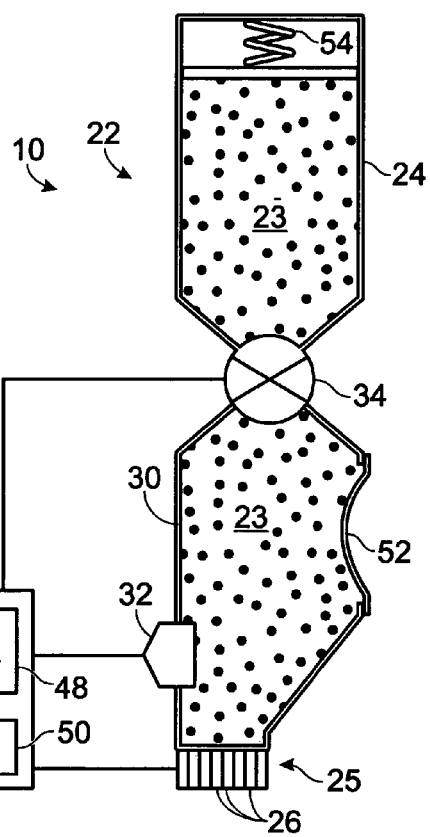
FIG. 2 is a schematic depiction of the inhaler of FIG. 1 according to an embodiment of the invention.

Turning now to FIG. 2, it will be noted that inhaler 10 may include an ejection apparatus 22 for ejecting droplets of fluid medicament 23. The ejection apparatus, in turn, may include a medicament supply 24, an ejector head 25 that includes a plurality of ejectors 26, and a controller 28 that may be configured to actuate the ejectors to dispense the medicament.

The controller may be configured to regulate the pressure of medicament at the ejectors. For example, the inhaler may include an accumulator 30 that defines an accumulator volume that may be in fluid communication with the ejectors, a sensor 32 that may be configured to sense pressure of the fluid within the accumulator, and a valve mechanism 34 that may be in fluid communication with the medicament supply. Controller 28 may be configured to operate valve mechanism 34 in response to the sensed pressure within the accumulator, thereby regulating pressure at the ejectors.

Figure 3:
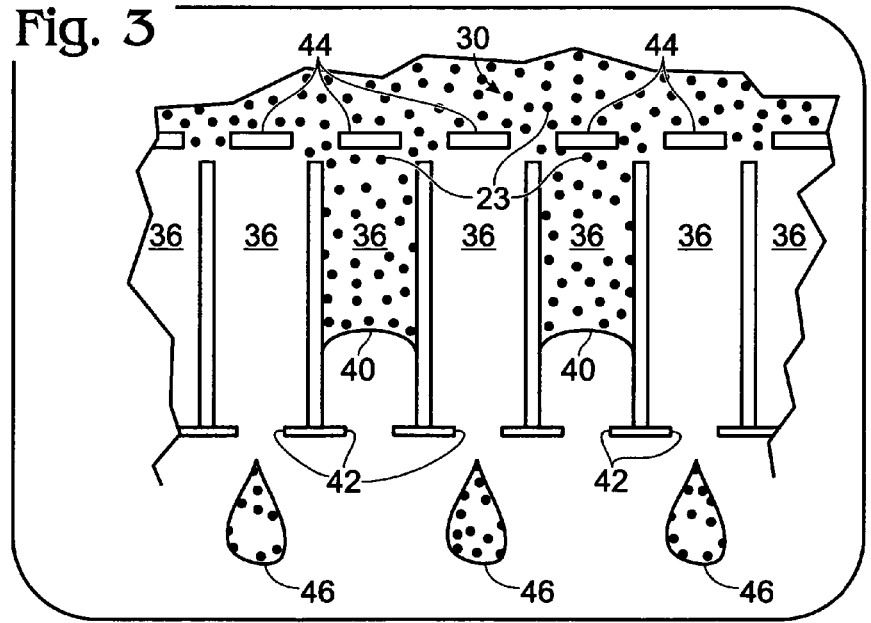
FIG. 3 is a depiction of the ejectors of the inhaler of FIG. 1 according to an embodiment of the invention.

The ejectors of the ejection apparatus typically serve to generate the medicament aerosol for inhalation by the user. As shown in greater detail in FIG. 3, each such ejector may include an ejector chamber 36 that is in fluid communication with accumulator 30. Medicament 23 thus may pass from the accumulator into the ejector chambers. Each ejector may be adapted to receive and contain a charge of medicament within its associated ejector chamber. This may be accomplished, in part, by the geometry of the ejectors, which may lead to formation of menisci 40 within the ejector chambers, typically adjacent to corresponding ejection orifices 42. Medicament generally does not pass through ejection orifices without en ejection event, due to the presence of such menisci.

Typically, each ejector includes at least one ejection element 44 configured to selectively and controllably eject medicament from within the corresponding ejector chamber as a medicament droplet 46. The ejection element (also referred to as a vaporization element) may take the form of a heating element opposite the ejection orifice. In this embodiment, in response to an ejection signal from controller 28 (e.g., a predetermined voltage applied across the heating element), the heating element may be activated, heating medicament in the vicinity of the heating element which, in turn, expands toward the ejection orifice, overcoming opposing forces of the meniscus and forcing medicament out of the ejection orifice in a predictably-sized droplet. The size and trajectory of such an ejected droplet may be reliably predicted based on the size and shape of the ejector, the ejector chamber, and the ejection orifice, the chemical composition of the medicament, as well as the power dissipated in the ejector chamber.

Once a droplet has been ejected, and the ejection element deactivated (e.g. cooled), medicament may again flow into the ejector chamber, effectively filling it with a new charge of medicament upon formation of a meniscus adjacent the ejection orifice.

Ejection element 44 may take any of various forms, including for example, a resistor, a piezoelectric transducer, a vibrating porous membrane, or any other structure capable of controlled activation by the inhaler's controller. In each case, the presently-described inhaler is typically able to produce an inhalant stream without the use of an aerosol carrier or propellant.

Controller 28 may be adapted to control inhaler 10 electronically, mechanically, or both. Controller 28 thus may include a processor 48 and a memory 50 configured to store preprogrammed operating parameters. Memory 50 may include volatile memory, nonvolatile memory, or both. User inputs, such as those indicated at 16 and 18 typically communicate with controller 28, for example, to provide processor 48 with information/direction regarding the dosage of medicament to be released. Such information may be provided by the user, or may be provided by a physician or pharmacist, either directly or indirectly.

Controller 28 may be in communication with ejectors 26 so as to provide control of ejection elements 44. Such direction may come in the form of an electronic signal directed to one or more ejection elements to effect activation of such element(s), and thus, to effect ejection of droplets of medicament. Thus, when a user depresses or otherwise activates the activation input 18, controller 28 may send an appropriate ejection signal to at least one ejection element 44. Upon receipt of such an ejection signal, an ejection element produces a droplet of medicament, as described above. Typically, the force of the expanding charge of medicament within an associated ejection chamber may be sufficient to successfully eject a droplet of medicament from the ejection chamber. The duration, intensity, and/or other characteristic of the electronic signal may be altered to effect changes in the medicament dosage and/or ejection characteristic, depending on the type of ejection element used, and the dosage desired.

Inhaler 10 may further include a power supply (not shown). The power supply may be a battery or other suitable power supply, whether disposable or permanent. In some cases it may be desirable for the power supply to be a replenishable power supply, such as a rechargeable battery.

The medicament pressure within accumulator 30 may be at least partially regulated by fluidically coupling the accumulator with a compliant member 52, as shown in FIG. 2. Compliant member 52 may be resilient (and/or elastic) so that as the inhaler is activated, and medicament is ejected from the ejection apparatus and pressure within the accumulator decreases, the compliant member 52 may deform elastically into the accumulator. This deformation may serve to regulate the back pressure within the accumulator. Alternatively, where the regulated pressure is a positive pressure, the compliant member may be deformed elastically outward during charging of the accumulator from the medicament supply, such that the compliant member relaxes as the inhaler is activated and accumulator pressure decreases.

Resilience of the compliant member may be provided by a spring bag, a rubber bladder, a diaphragm, or other suitable mechanism. Furthermore, the compliant member need not be a discrete component of the inhaler. For example, the accumulator itself may function as a compliant member. The accumulator may be manufactured from a sufficiently resilient material that the body of the accumulator itself serves to regulate the pressure within the accumulator. Where the ejection mechanism used in ejection apparatus 22 may perform satisfactorily under positive fluid pressure, the compliant member may be configured to provide a regulated positive pressure within the accumulator, rather than a negative back pressure.

By regulating the medicament pressure at the ejector, operation of the inhaler may be rendered relatively insensitive to the orientation of the inhaler itself. That is, the inhaler may operate efficiently even when held at an angle. By monitoring fluid pressure within the accumulator, the inhaler controller may also be configured to permit detection of low medicament levels, and to disable operation of the inhaler before adverse effects of operation without medicament can occur. In addition, regulation of fluid pressure may permit at least some control of drop size produced by the ejector, as discussed below.

The action of the compliant member may assist in eliminating short-term surges (or 'spikes') in medicament pressure, and therefore may help regulate the fluid being delivered to the ejectors. In one embodiment, the compliant member takes the form of a resilient diaphragm separating the outside atmosphere from the medicament fluid contained within the accumulator. Such a diaphragm is typically selected so that the size and resilience of the diaphragm results in an operating pressure range that permits the inhaler to deliver at least one dose of medicament without replenishing the medicament within the accumulator via valve 34.

The accumulator may be fluidically coupled to the outlet of valve mechanism 34, which valve mechanism opens and closes in response to variations in the measured pressure within accumulator 30. Any valve mechanism that permits the regulated addition of medicament to the accumulator volume from the medicament supply may be an appropriate valve mechanism for the purposes of this disclosure. A variety of such valve mechanisms are commercially available and selection of a particular design for a specific implementation would be within the purview of a person skilled in the art. For example, appropriate valve mechanisms may include peristaltic valves ("pinch valves"), solenoid valves, or any other valve that can be actuated automatically.

It should be appreciated that while the valve mechanism may be such that the valve mechanism is either open or closed, valve mechanisms with variable flow control can be substituted for an "on/off" valve mechanism.

Valve mechanism 34 may be an electronically controlled valve. In particular, small solenoid-activated fluid valves are appropriate valve mechanisms for use in the disclosed inhaler. If a smaller valve with reduced power requirements is desired, any of a variety of fabricated microvalves may be employed. By microvalve is meant a mechanical device that controls the flow of fluid in a micro-scopic channel. Microvalves may be actuated by applied electrostatic force, magnetic force, or piezoelectric forces. Microvalves may be formed, for example, by thin film deposition, microlithography, micromachining, or a combination thereof.

The inlet of valve 34 may be fluidically coupled to fluid medicament supply 24. When the backpressure in the accumulator reaches a minimum acceptable value, valve mechanism 34 may be opened, fluidically connecting the accumulator to the medicament supply. Medicament may then flow into the accumulator, increasing the medicament pressure. When the backpressure is greater than a second, acceptable value, the valve mechanism may close. In this way, valve mechanism 34 and compliant member 52 may act as an active pressure regulation mechanism. Typically, the medicament within accumulator 30 may be maintained at a pressure that varies within the operational limits of ejectors 26, regardless of the pressure within the medicament supply.

As indicated above, sensor 32 may be positioned to measure pressure within the accumulator. The sensor may be configured to measure pressure directly, or may be configured to measure the volume defined by the accumulator and compliant member, and thereby measure the pressure indirectly. The sensor may communicate measurements to controller 28, so that valve mechanism 34 may be operated when needed. In one embodiment, the sensor is a pressure sensor disposed adjacent to the ejector head 25, so that the pressure measured by the sensor closely corresponds to the fluid pressure at the ejectors. This may help to ensure that the fluid pressure adjacent the ejectors lies within operational parameters stored in the controller. The fluid pressure may be sensed continuously, sensed at discrete intervals, or sensed in response to specified actions of the controller or of the user.

The medicament supply may be integrated with the accumulator and the ejectors, or may be separate and/or removable. In particular, it may be useful to utilize a medicament supply that may be removed and replaced, for example, when refilling a prescription. It also may be useful to employ a medicament supply which is fluidically efficient. That is, a medicament supply typically may be emptied substantially completely, leaving little medicament in the medicament supply once low pressure renders the inhaler unusable.

The fluid supply may include a pressurizing element 54, so that the medicament supply may be pressurized. Pressurization of the medicament supply may ensure that sufficient medicament may be provided to the valve mechanism upon demand to efficiently fill the accumulator volume. The medicament supply may be pressurized using a variety of methods. The medicament supply may include a pressurizing gas, or it may include a spring-loaded collapsible reservoir (as depicted in FIG. 2), or a gas pressurized elastomer or rolling diaphragm bag. Where the fluid supply includes a rolling diaphragm bag, it may be useful to utilize a flat spring, or 'constant force' spring, so that the pressure applied to the bag may be held substantially constant as the bag empties. Although a variety of pressurized medicament supplies have been discussed, it should be appreciated that a medicament supply that permits the medicament to be actively pumped, or to flow gravimetrically into the accumulator may also be employed.

The ejectors may be manufactured using photolithographic or other micromachining methods known in the art, including any desired combination of photoresist deposition, etching, ablation, pattern deposition, plating, and so forth. Although such manufacturing processes are selected to produce highly consistent ejectors, normal variation in the manufacturing processes may produce variation in the output characteristics of individual ejectors. That is, ejectors prepared using substantially the same manufacturing process may produce drops of different sizes under the same operating parameters. As the dosage provided by a medicament inhaler may be dependent upon the size of drops produced, ejectors that produce drops having sizes different than the desired or expected drop size may in turn yield medicament dosages that differ from the calculated and expected dosage. Such variant ejectors may be unsuitable for use, resulting in a waste of raw material and manufacturing time.

To avoid such expense, ejector mechanisms may be screened during manufacture of the inhaler to evaluate one or more output characteristics of the ejectors. The output characteristics may then be compared to expected or target output characteristics, and a determination made as to whether the ejector's output characteristics are within a defined tolerance range of the desired output characteristics.

An output characteristic that may be useful for evaluating the output of the ejectors is ejected drop volume. The ejector mechanism may have a target drop volume or may have multiple target drop volumes, for example where a plurality of target drop volumes is desired in order to target simultaneous discreet locations in the respiratory tract of the patient. Generally the volume of an ejected drop is difficult to measure directly, and so the size of the generated drops may be measured indirectly by determining weight of ejected drops. The weight of a known number of deposited drops may be determined accurately, and so the weight per ejected drop may be calculated. As used herein, drop size may mean drop volume, drop weight, or both.

The tolerance range for ejected drop size may be narrow, such as plus or minus 5% or 10%, for example. Alternatively, the tolerance range may be broader, such as plus or minus 20% or 50%. The accuracy of the ejector in producing the desired drop size may be particularly important due to variations in medicament absorption for different drop sizes.

Where an ejector's output characteristics are determined to lie outside of a defined tolerance range, a correction factor may be determined for application to the operational parameters used by the ejector to form the ejected droplets. The correction factor may then be incorporated into the instructions encoded in the inhaler controller. The correction factor may be calculated such that, when the correction factor is applied to the operational parameters of the inhaler, the resulting output characteristics of the inhaler will fall within the desired tolerance range of output characteristics.

A correction factor may be applied to any operational parameter and/or aspect of the operation and actuation of the ejector that may influence the selected output characteristic. The correction factor may be applied on a consistent basis, for example the correction factor may be selected so as to adjust the average drop size produced by the ejector throughout the subsequent operation of the inhaler. Alternatively, or in addition, the correction may be variable and/or time dependent, for example a variable correction factor may be applied over the course of a particular ejector firing sequence.

As an example, ejected drop size may be influenced by correction factors applied to a number of operational parameters. The construction of the ejector itself, including but not limited to the size of the ejector chamber, the size of the ejector orifice, and the area of the ejection element, may each effect the drop sizes produced. The ejector typically is designed so that upon ejection of a drop, capillary forces cause medicament to refill the ejector and draw a new charge of medicament into the ejector chamber. These capillary forces pull against the backpressure of the medicament in the accumulator. Depending upon the design of the ejector itself, the meniscus of the medicament may overshoot its equilibrium position, and therefore quickly pull back in response to the typically negative pressure of the medicament supply in the accumulator. This movement of the medicament meniscus may be referred to as "ringing", and after a few cycles of movement, the meniscus may return to the equilibrium position. The ejector apparatus may be intentionally under-damped to increase the speed with which the medicament refills the ejector. Alternatively, the ejector apparatus may be over-damped, to minimize ringing and increase consistency in drop size.

In addition, the physical properties of the medicament may effect the operation of the ejector and therefore the drop size, such as medicament viscosity, vapor pressure, etc. The drop size produced by an ejector may change during a sequence of repeated firings. For some ejectors, the drop size will tend to increase due to thermal warming of the ejector. The frequency of firing may also effect ejected drop size, particularly for an over-damped drop generator, which may exhibit decreased drop sizes with increasing firing frequency, as the ejector has less time to refill with medicament. Ejected drop size also may decrease as the pressure of the medicament at the ejector decreases. However, drop size may increase with an increasing temperature of the ejector.

Selected identified operational parameters may be well-suited for consistent, or static correction intended to effect the average drop size produced by the inhaler during operation. Alternatively, some operation parameters may be varied dynamically during the course of the ejection sequence. In addition, although any operational parameter that influences drop size or total drop number is a suitable operational parameter for application of a correction factor, it may be most economical to vary those operational parameters that may be directly or indirectly effected by the controller, either singly, or in combination. For example, each ejection element of the inhaler may be controlled independently, in groupings, or in selected subsets of the full ejector set. The controller may also electronically control the rate of ejection element activation. It may be possible to apply a correction factor to either the rate of droplet generation, or the number of ejectors firing, in order to control the medicament dosage produced by the inhaler. The delivered dosage may be regulated by any appropriate combination of firing rate and quantity control.

The alteration of some operational parameters may result in multiple simultaneous or sequential effects on the medicament dosage, and such effects may be additive or subtractive. For example, increasing the number of drops ejected during a burst increases medicament dosage, while ejector warming during the burst also tends to increase ejected drop size. Similarly, increasing ejection frequency may produce decreased drop size, but thermal effects may at the same time increase ejected drop size, as during a sequence of rapidly repeated ejections, the ejector itself may grow warmer, resulting in an increase in the volume of the ejected drops. Where this warming effect is undesirable, it may be at least mitigated by altering the ejector firing frequency either statically (setting a lower consistent firing rate), or dynamically (progressively reducing the firing rate over the course of a firing sequence). The contribution of each operation parameter may be considered when determining the correction factor to be employed so as to fall within the desired tolerance range of the selected output characteristic, alternatively one or more of the contributions to the dosage adjustment may be deemed minimal, and therefore not considered when determining an appropriate correction factor.

Once an appropriate correction factor or combination of correction factors has been calculated that will at least substantially compensate for the deviation of the output characteristics of the ejector from the desired output characteristics, the correction factor or factors may be encoded into the controller. Specifically, the instruction encoded in memory 50 and/or processor 48 may be altered so as to incorporate the calculated correction factor into the operational parameters of the inhaler as applied by the controller. Subsequently, actuation of the inhaler may produce an appropriate dosage of the fluid medicament. In this case appropriate dosage may refer to an appropriate drop size of medicament ejected, an appropriate total amount of medicament ejected, ejection of droplets of an appropriate size for retention in the lungs, or any combination thereof.

An exemplary process of screening and calibrating a medicament inhaler is set out in flowchart 60 of FIG. 4. As set out in the exemplary process, the inhaler is first manufactured, assembled, and filled with the desired medicament fluid, at 62. As part of the screening process, the ejector of the inhaler is actuated, at 64, generating output drops. The output of the ejector is then characterized by testing the drop weight as a function of the drop frequency, at 66. As discussed above, drop weight may increase as the ejector fires, due to warming effects, but may also decrease as firing frequency increases, due to a decreased fluid pressure at the ejector nozzles. The effect of both firing frequency and ejector temperature on drop weight is then determined, at 68. An appropriate pressure value for the medicament is then determined and encoded onto the controller, at 70.

As discussed above, inhaler 10 may incorporate passive or active pressure regulation, and where the controller actively regulates medicament pressure, the application of a correction factor to the regulated pressure value of the medicament may produce a corrected average drop weight. For example, a more negative pressure at the ejector may reduce the volume of the drops produced by that ejector. Alternatively, where a greater drop volume is desirable in order to attain a desired output characteristic, the medicament pressure at the ejector may be increased. Alternatively, or in addition, the applied correction to the medicament pressure may be variable. Although medicament pressure is typically maintained at a negative gauge pressure to prevent seepage of medicament from the ejector orifices, the inhaler may be configured so that the medicament pressure becomes positive during drop ejection events, thereby increasing ejected drop size, while returning to a negative pressure when the ejection event is complete.

The desired drop frequency as a function of the number of drops ejected may be determined and encoded onto the controller as well, at 72 of FIG. 4. For example, varying the firing frequency during a sequence of ejector firings may result in greater consistency in ejected drop volumes over the course of the ejection sequence. Alternatively, firing frequency may be dynamically varied so that the effect of warming on the ejector produces increasing drop weights over the course of a corrected ejector firing sequence.

Upon applying a correction factor to yield a desired drop frequency as a function of drop number, the resulting dosage upon actuation of the inhaler may be compared to the target output dosage, at 74. If the dosage is within the range of acceptable values, this target value may be encoded onto the controller, at 76, and all dosage values generated by the inhaler may be based on a nominal drop weight. If the dosage is not within the nominal target range, the actual drop weight produced by the inhaler may be encoded onto the controller, at 78, and all dosage values generated by the inhaler may then be based upon the actual drop weight produced by the inhaler. For example, changes to the dispensed medicament dosage may be made, for example, by varying the number of ejectors utilized, the number of drops generated, etc., based upon the encoded drop weight, rather than the target drop weight, resulting in more accurate delivery of medicament.

The calibration of the disclosed inhaler may also be more generally described as set out in flow chart 90 of FIG. 5. The medicament inhaler is manufactured at 92. The output of the inhaler may then be characterized, at 94, and the characterized output compared to the target output characteristics, at 96. A correction factor may then be determined to produce the target output from the inhaler, at 98. Then the controller may be configured to apply the correction factor to the inhaler, at 100.

While various alternative embodiments and arrangements of an inhaler, and methods of manufacturing, calibrating, and using an inhaler have been shown and described above, it will be appreciated by those of skill in the art that numerous other embodiments, arrangements, and modifications are possible and are within the scope of the present disclosure. Those skilled in the art thus will understand that many variations may be made therein without departing from the spirit and scope as defined in the following claims. The present description should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application.

What is claimed is:

1. A medicament dispenser, comprising:
a medicament supply;
an ejector having a performance characteristic, the ejector being in fluid communication with the medicament supply;
an accumulator for storing medicament in fluid communication with the ejector;
a sensor configured to sense medicament pressure within the accumulator;
a valve intermediate the medicament supply and the accumulator, the valve configured to open and close in response to a sensed medicament pressure within the accumulator to regulate medicament pressure at the ejector; and
a controller configured to actuate the ejector using an operational parameter to produce a plurality of medicament drops having target drop characteristics, the operational parameter including a correction factor based on the performance characteristic of the ejector.

2. The medicament dispenser of claim 1, further comprising a compliant member that regulates pressure within the accumulator.

3. The medicament dispenser of claim 1, wherein the controller is configured to operate the valve to increase the medicament pressure within the accumulator.

4. The medicament dispenser of claim 1, wherein the performance characteristic of the ejector includes ejected drop volume.

5. The medicament dispenser of claim 1, wherein the performance characteristic of the ejector includes ejected drop weight.

6. The medicament dispenser of claim 1, wherein the operational parameter includes drop ejection frequency.

7. The medicament dispenser of claim 1, wherein the operational parameter includes number of drops ejected.

8. The medicament dispenser of claim 1, wherein the operational parameter includes medicament pressure.

9. The medicament dispenser of claim 1, wherein the operational parameter includes ejector temperature.

10. The medicament dispenser of claim 1, wherein the operational parameter includes a static correction factor.

11. The medicament dispenser of claim 1, wherein the operational parameter includes a dynamic correction factor.

12. An inhaler, comprising:
a medicament supply;
a medicament accumulator for storing medicament in fluid communication with the medicament supply;
a compliant member fluidically coupled to the medicament accumulator;
a valve intermediate the medicament supply and the medicament accumulator;
a sensor configured to sense a medicament pressure within the medicament accumulator;
an ejector in fluid communication with the medicament accumulator, wherein the ejector has a performance characteristic; and
a controller configured to apply a correction factor to an operational parameter of the ejector, wherein the correction factor is determined by the performance characteristic of the ejector.

13. A method of calibrating a medicament inhaler to a target output characteristic, the medicament inhaler having a medicament supply, a medicament accumulator for storing medicament in fluid communication with the medicament supply, a sensor configured to sense medicament pressure within the accumulator, a valve intermediate the medicament supply and the medicament accumulator, a medicament ejector in fluid communication with the medicament accumulator, and a controller configured to open and close the valve in response to a sensed medicament pressure within the accumulator, the method comprising:
manufacturing the medicament inhaler;
characterizing the output of the inhaler;
comparing the characterized output to the target output characteristic;
determining a correction factor to produce the target output from the inhaler; and
configuring the controller to apply the correction factor to the inhaler.

14. The method of claim 13, wherein characterizing the output of the inhaler includes determining an ejected drop weight.

15. The method of claim 14, wherein characterizing the output of the inhaler includes determining the ejected drop weight as a function of drop frequency.

16. The method of claim 14, wherein characterizing the output of the inhaler includes determining the ejected drop weight as a function of medicament ejector temperature.

17. The method of claim 13, wherein comparing the characterized output to the target output characteristic includes comparing a determined ejected drop weight to a target drop weight.

18. The method of claim 13, wherein determining a correction factor includes determining a corrected drop weight.

19. The method of claim 13, wherein configuring the controller to apply the correction factor to the inhaler includes configuring the controller to apply a static correction factor.

20. The method of claim 13, wherein configuring the controller to apply the correction factor to the inhaler includes configuring the controller to apply a dynamic correction factor.

21. The method of claim 13, wherein configuring the controller to apply the correction factor to the inhaler includes configuring the controller to apply a corrected drop ejection frequency.

22. The method of claim 13, wherein configuring the controller to apply the correction factor to the inhaler includes configuring the controller to apply a corrected number of drops ejected.

23. The method of claim 13, wherein configuring the controller to apply the correction factor to the inhaler includes configuring the controller to apply a corrected medicament fluid pressure.

24. The method of claim 13, wherein configuring the controller to apply the correction factor to the inhaler includes configuring the controller to apply a corrected ejector temperature.

25. The method of claim 24, wherein configuring the controller to apply the corrected ejector temperature includes configuring the controller to apply a corrected drop ejection frequency.

26. An inhaler, comprising:
- a means for supplying fluid medicament;
- a means for ejecting fluid medicament, the means having a performance characteristic;
- a means for accumulating and storing fluid medicament in fluid communication with the ejector means;
- a means for sensing fluid medicament pressure within the accumulating means;
- a means for regulating an addition of medicament to the accumulating means from the fluid medicament supply means in response to the pressure sensing means; and
- a means for actuating the ejector means using an operational parameter calculated from the performance characteristic of the ejector means.

\* \* \* \* \*